United States Patent [19]

Tsukahara

[11] Patent Number: 5,064,353
[45] Date of Patent: Nov. 12, 1991

[54] PRESSURE RESPONSIVE LINEAR MOTOR DRIVEN PUMP

[75] Inventor: Kinji Tsukahara, Seki, Japan

[73] Assignee: Aisin Seiki Kabushiki Kaisha, Aichi, Japan

[21] Appl. No.: 474,325

[22] Filed: Feb. 2, 1990

[30] Foreign Application Priority Data

Feb. 3, 1989 [JP] Japan ................................ 1-25371

[51] Int. Cl.$^5$ ..................... F04B 49/00; G05B 11/00
[52] U.S. Cl. ..................................... 417/383; 417/45; 417/417; 417/18; 623/3; 600/16; 600/17
[58] Field of Search ................. 417/18, 45, 417, 383; 623/3; 600/16, 17

[56] References Cited

U.S. PATENT DOCUMENTS

| | | | |
|---|---|---|---|
| 3,966,358 | 6/1976 | Heimes et al. | 623/3 |
| 4,163,911 | 8/1979 | Simes et al. | 417/417 |
| 4,173,796 | 11/1979 | Jarvik | 623/3 |
| 4,334,180 | 6/1982 | Bramm et al. | 600/17 |

Primary Examiner—Richard A. Bertsch
Assistant Examiner—David W. Scheuermann
Attorney, Agent, or Firm—Burns, Doane, Swecker & Mathis

[57] ABSTRACT

Pumping apparatus which compresses or decompresses an actuating fluid alternately, which is in turn used to pump an artificial heart. To reduce the size of the apparatus, a diaphragm which contains a non-compressible actuating liquid is driven reciprocatingly by an electric linear motor. To prevent the occurrence of an excessive suction pressure which may be caused by the non-compressibility of the actuating fluid, at the commencement of the suction interval, the current to energize the linear motor is increased gradually and the pressure of the actuating liquid is detected. When the liquid pressure goes out of a selected safety range, the gradual increase ceases. A discharge stroke is detected from an integrated value of the motor current during the discharge interval, and when it reaches a given value, a reversal of the direction of energization of the motor is initiated.

7 Claims, 8 Drawing Sheets

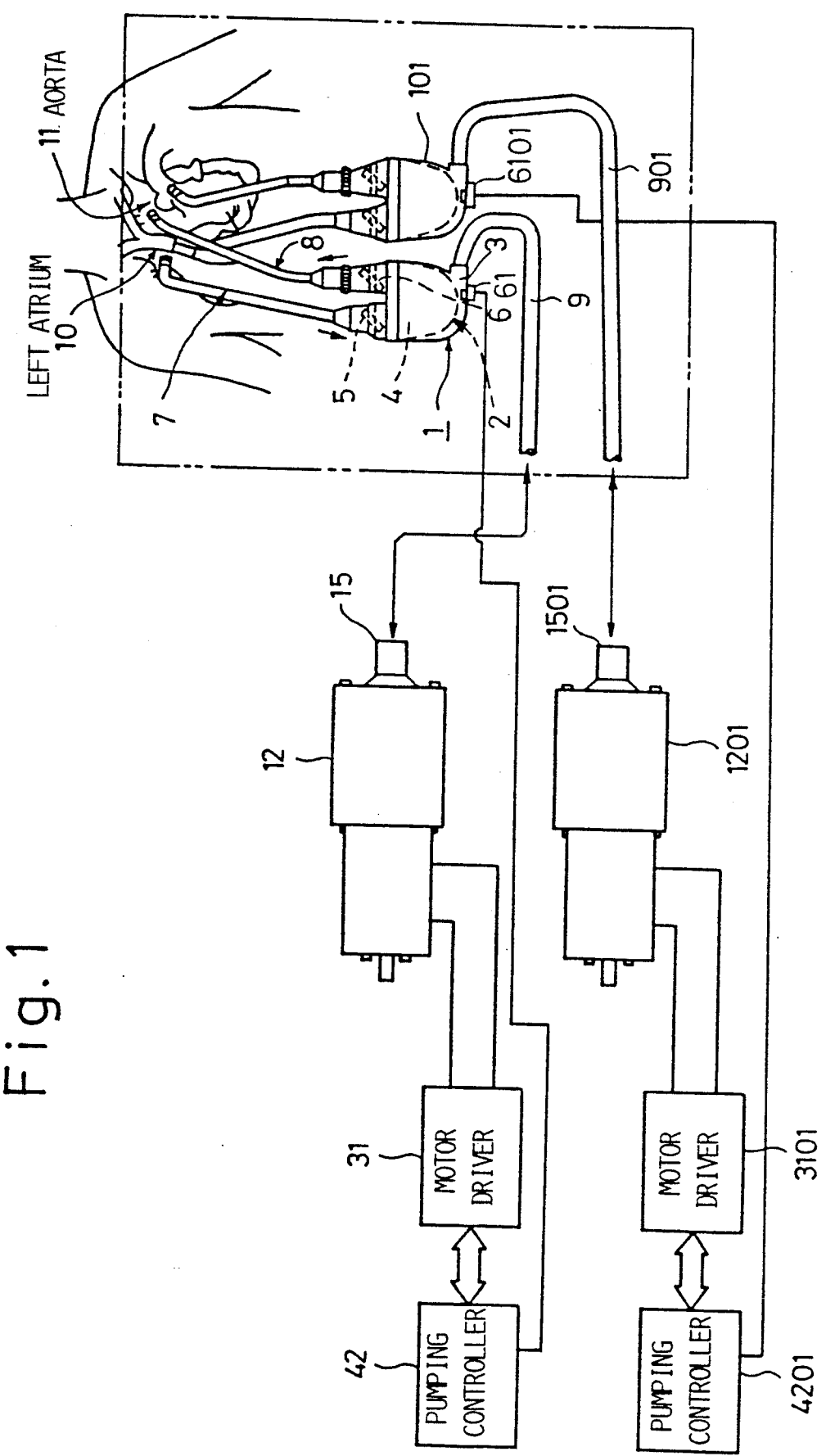

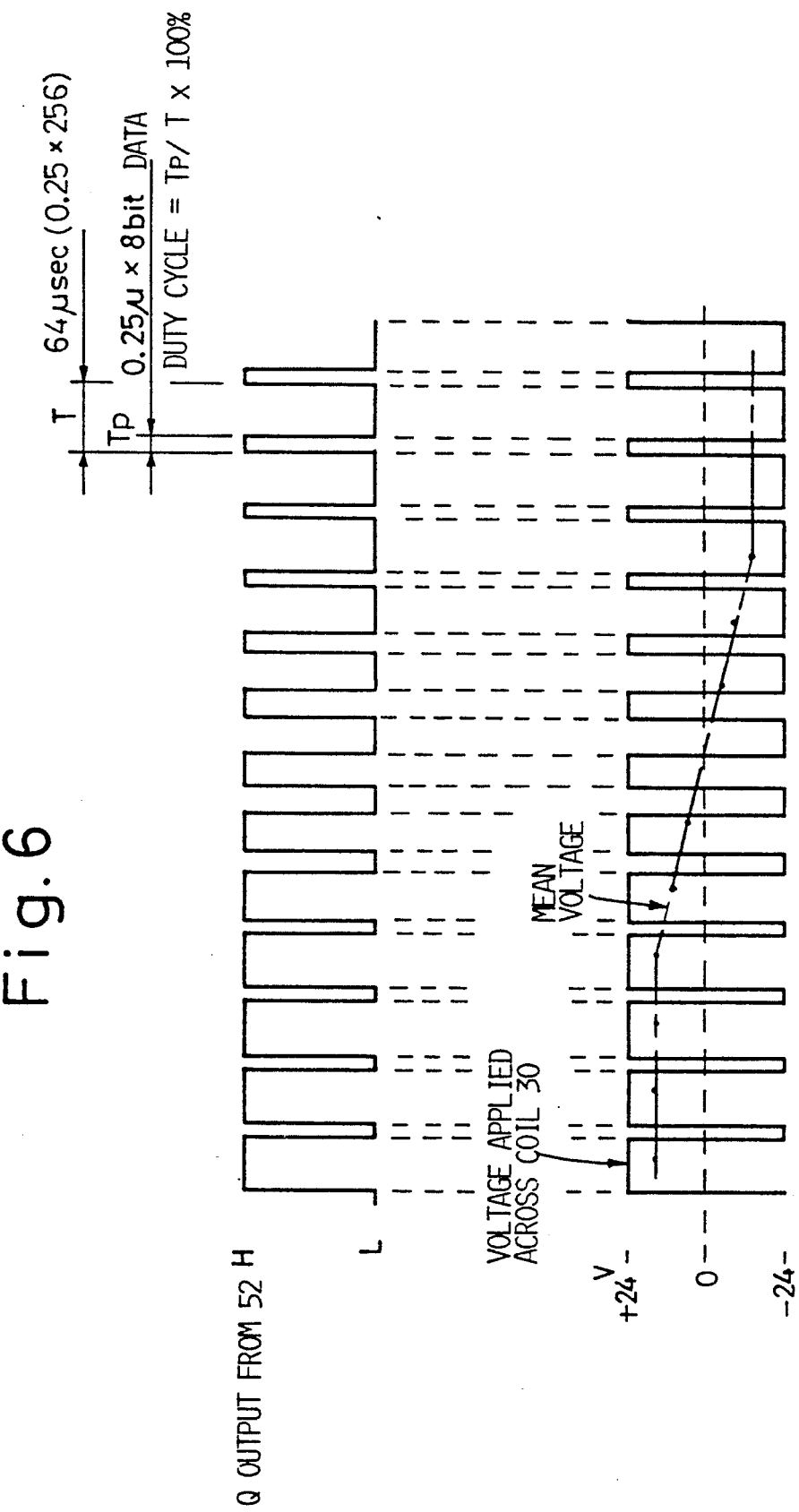

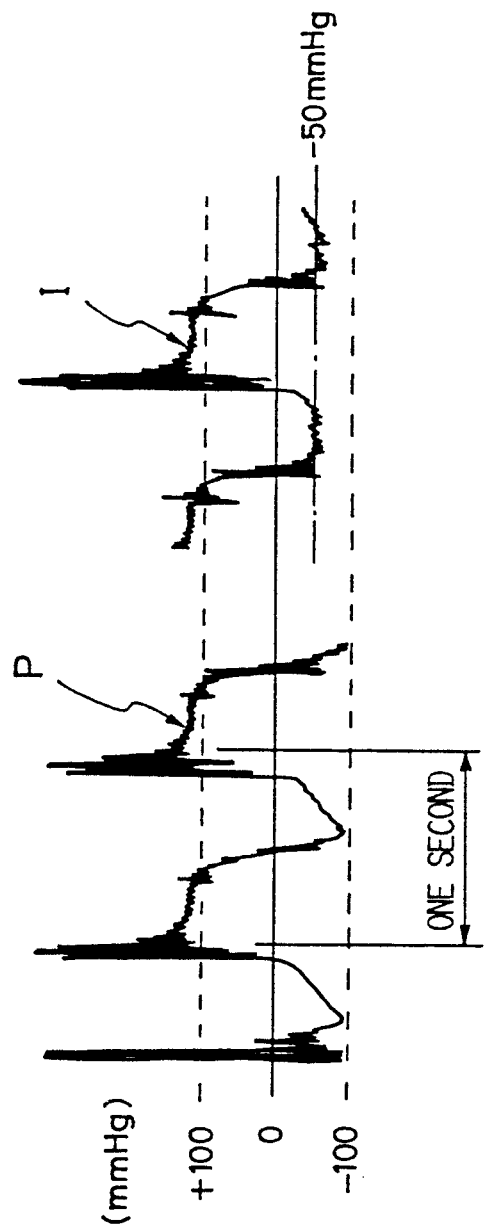

PRESSURE RESPONSIVE LINEAR MOTOR DRIVEN PUMP

FIELD OF THE INVENTION

The invention relates to a liquid pump which utilizes an electric linear motor to drive a reciprocable member.

PRIOR ART

An artificial heart comprises an outer vessel having an operation chamber in which a diaphragm is disposed to divide the interior of the vessel into a blood chamber and an actuating chamber, to which a high pressure such as air of high pressure and a low pressure, acting as a suction pressure, are alternately supplied. The blood chamber is alternatively connected to a suction port through a first check valve and communicates with a discharge port through a second check valve. When a high pressure is supplied to the actuating chamber, the diaphragm is pressurized, tending to deflate the blood chamber, whereby a fluid in the blood chamber, namely, blood, is discharged to the discharge port through the second check valve. When the actuating chamber is switched to a low pressure, the diaphragm is sucked into the actuating chamber, tending to inflate the blood chamber, whereby the fluid or blood is drawn into the blood chamber from the suction port through the first check valve. Accordingly, by alternately supplying a positive and a negative pressure to the actuating chamber of the artificial heart, the latter draws the fluid or blood through the suction port and discharges it to the discharge port. The artificial heart is driven by alternately supplying the high and the low pressure (air) to the actuating chamber.

In the prior art practice, an air pumping apparatus is used to supply such high and low pressure (air). As disclosed in Japanese Laid-Open Patent Applications No. 99,967/1983 and No. 169,460/1983, such pumping apparatus comprises an electric motor, an air pump driven by the motor, a high pressure accumulator to which a discharged pressure from the pump is supplied, a low pressure accumulator which feeds a suction pressure to the pump, a high pressure and a low pressure solenoid valve which selectively connect either the high pressure or the low pressure accumulator to the actuating chamber of the artificial heart. When the low pressure valve is closed while the high pressure valve is opened, an air of high pressure is supplied to the actuating chamber of the artificial heart. On the other hand, when the high pressure valve is closed while the low pressure valve is open, a low pressure or suction pressure may be supplied to the actuating chamber.

It will be seen that a conventional pumping apparatus of the kind described includes a number of mechanical elements including the electric motor, the air pump, the accumulators and the high and the low pressure solenoid valve. Since the accumulator requires a relatively large space, the overall apparatus becomes bulky. If an attempt is made to eliminate the accumulators by providing a reciprocating air pump which is designed to supply a high pressure (discharge pressure)/low pressure (suction pressure) to the artificial heart directly, the compressibility of the actuating fluid, which is air, requires a volumetric shrinkage and expansion of the actuating fluid, which results in a reduced magnitude of a change in the air pressure achieved relative to a reciprocating stroke of the pump. In addition, a pressure rise when switching from the suction to the discharge stroke as well as a pressure fall when switching reversely become delayed, thus presenting a need to provide an air pump having a relatively high output.

Japanese Laid-Open Patent Application No. 28,969/1984 discloses a pumping apparatus which utilizes a linear motor to intermittently pressurizes a bag containing a gas or liquid which is to be supplied to an actuating fluid chamber of an artificial heart. In this disclosure, a high and a low pressure solenoid valve can be dispensed with, thus reducing the number of mechanical elements required. However, where a gas is used as an actuating medium, the compressibility thereof also involves a time delay in the pressure rise and the pressure fall when switching from the suction to the discharge stroke or vice versa. In addition, the actuating fluid has a pressure absorbing capability, which prevents the volumetric size of the apparatus from being reduced. When a non-compressible fluid or liquid is used as an actuating fluid, a pressure rise or fall during the switching between the suction and the discharge stroke takes place rapidly, and such fluid has no capability to absorb the pressure, thus allowing the volumetric size of the apparatus to be reduced considerably.

However, when a silicone oil, for example, is used as a non-compressible actuating liquid to pump an artificial heart, it may result that during a suction stroke of the artificial heart or the pumping apparatus, the magnitude of the negative pressure rises very rapidly, and hence a canula which introduces a living blood to be coupled to the heart of a living body into the artificial heart will exhibit a rapid rise in its blood drawing capability, which combined with the non-compressibility of the actuating medium, results in a certain tissue of the living body may be drawn into the canula, if the rate at which the blood of the living body is collected to the distal end of the canule is slow relative to such rapid rise or if such tissue is located very close to the distal end of the canule. Upon such occurrence, the amount of blood which is drawn into the canula will be reduced, which in turn further increases the drawing action exerted upon the tissue of the living body, eventually causing a damage thereof.

SUMMARY OF THE INVENTION

It is an object of the invention to reduce the number of mechanical elements and to reduce the volumetric size of a pumping apparatus while simultaneously preventing the occurrence of an excessively high suction pressure and/or discharge pressure which may be caused by a relatively high pumping rate.

In accordance with the invention, the above object is accomplished by providing a pumping apparatus comprising a liquid pump (12) including an electric linear motor (25 to 30), and a reciprocable member (17, 18) communicating with a fluid output port (15) and driven for reciprocating motion by the motor to deflate/inflate a fluid space (50) in which a non-compressible liquid is contained; pressure detecting means (61) for detecting a pressure which prevails at the liquid output port (15); energization means (31) for alternately energizing an electric coil (30) to a positive and a negative polarity; and current control means (43) for defining the current level at which the energization to the positive and the negative polarity takes place and controlling the current flow in a manner such that during at least part of the energization to the negative polarity, which is used for suction stroke, the current level which is used to energize the coil is allowed to increase gradually to a given value through the energization means (31), but that the gradual increase is interrupted whenever a pressure detected by the pressure detecting means (61) during the gradually increasing process goes out of a given range. It is to be understood that the numerals appearing in the parentheses refer to elements of an embodiment to be described later in connection with the drawings.

When the pumping apparatus is used to drive an artificial heart, for example, the liquid pump (12) which is driven by the linear motor operates to supply a high pressure (discharge pressure) and a low pressure (suction pressure) to the actuating chamber of an artificial heart through the fluid output port (15) by means of the non-compressible liquid, which is silicone oil in the embodiment described later, in an alternate fashion. This takes place by causing the energization means (31) to energize the coil (30) of the liquid pump (12) to the positive and the negative polarity alternately. When the pump (12) supplies the non-compressible actuating liquid to the artificial heart, both a pressure rise when a switching from the suction to the discharge stroke as well as a pressure fall when switching from the discharge to the suction stroke take place rapidly, and the actuating fluid has no pressure absorbing capability. Accordingly, certain elements which are used in a conventional pumping apparatus such as accumulators and high and low pressure solenoid valves can be dispensed with, thus reducing the number of elements as well as the volumetric size of the pumping apparatus.

It is to be noted that when the pumping apparatus is used to drive an artificial heart, if the rate at which the blood is collected to the distal end of the canula is slow and/or tissues of a living body are located too close to the distal end of the canule, during the suction stroke of the pumping apparatus, a volumetric shrinkage of the space of the actuating liquid chamber of the heart may be retarded relative to the rate at which the suction pressure from the output port of the pumping apparatus rises, thus causing the suction pressure from the output port of the actuating liquid chamber to be increased. However, the suction pressure is detected by the pressure detecting means (61), and if such pressure goes out of a given range, the current control means (43) operates to interrupt a gradual increase in the current level which is used to energize the coil to the negative polarity, thus inducing a reduction in the rate at which the suction pressure rises. In other words, the suction rate is automatically slowed down automatically in a manner corresponding to the blood collection. Thus, a tendency that tissues of the living body may be unduly attracted to the canule to be eventually damaged can be reduced.

Other objects and features of the invention will become apparent from the following description of an embodiment thereof with reference to the drawings.

BRIEF DESCRIPTION OF THE DRAWINGS

FIG. 1 is a side elevation of an apparatus according to one embodiment of the invention, also schematically illustrating an associated arrangement;

FIG. 2b is a cross section, taken along the line IIB—IIB shown in FIG. 2a;

FIG. 6 graphically shows an output Q from a flipflop 52 shown in FIG. 3 in relation to a voltage applied to an electric coil 30 of the linear motor 12 in the form of a timing chart; and FIG. 7 graphically shows a detected pressure from a pressure sensor 61 shown in FIG. 1, a curve I indicating the detected pressure when the current level at which the coil is energized ceases to be changed in a manner corresponding to the detected pressure in accordance with the invention, and a curve P indicating the corresponding detected pressure which occurs when such control is not made.

DETAILED DESCRIPTION OF EMBODIMENT

Figure 2A:
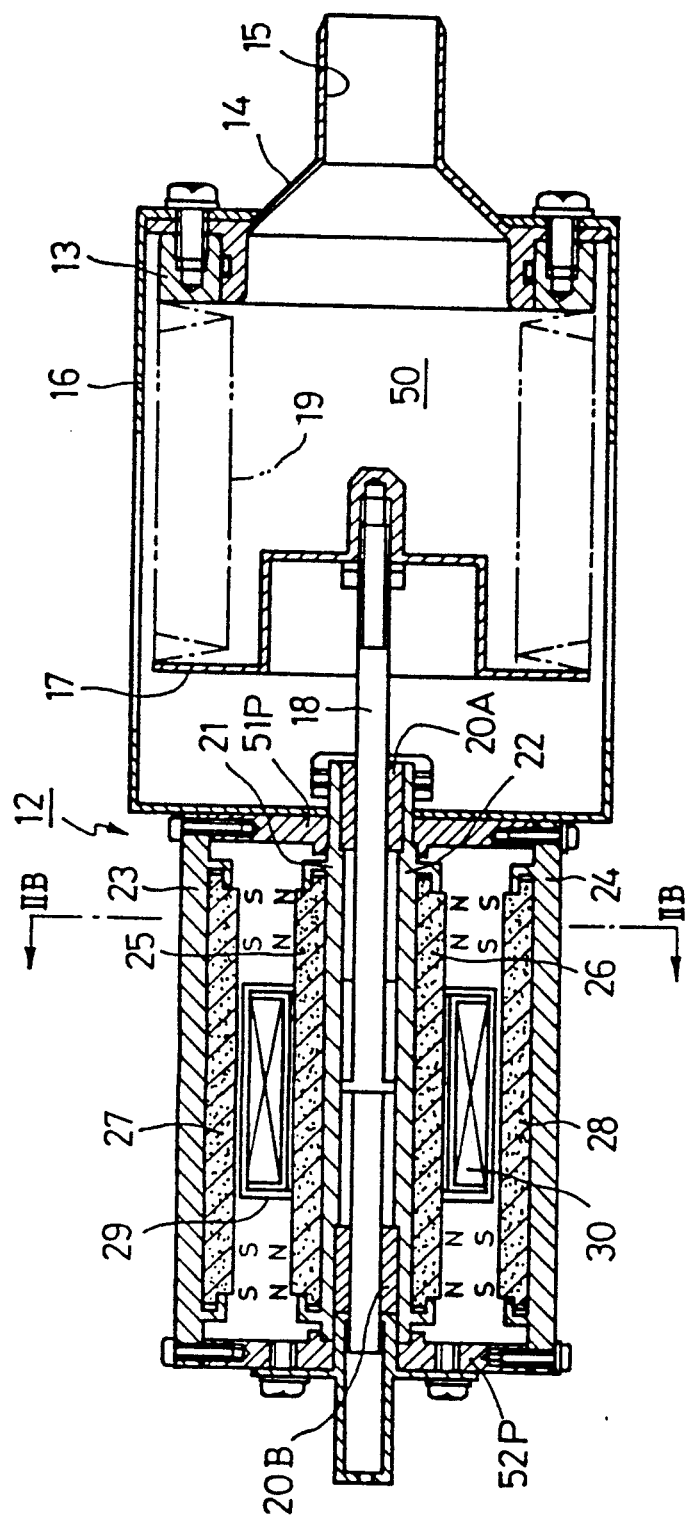
FIG. 2a is a longitudinal section, to an enlarged scale, of a liquid pump 12 shown in FIG. 1.

FIG. 1 shows a manner of coupling one embodiment of the invention to an artificial heart. The artificial heart 1 includes a diaphragm 2 disposed in an actuating chamber 3 which is located within an outer vessel. The construction of the heart 1 is known in itself in that a first canule 7 communicates with an internal space 4 of the diaphragm 2 through a suction check valve 5 and a second canule 8 communicates with the internal space through a discharge check valve 6. Under the condition shown, the first canule 7 is connected to a left atrium 10 while the second canule 8 is connected to aorta 11. The actuating chamber 3 of the heart 1 in which silicone oil is contained is connected to an output port 15 of a fluid pump 12 which is driven by a linear motor through a tubing 9. A pressure sensor 61 detects a pressure which prevails in the actuating chamber 3 so that a voltage of a level which depends on the detected pressure may be supplied to a pumping controller 42.

FIG. 1 shows another set of artificial heart 101 which is also connected to the heart of the living body. The heart 101 also includes an actuating chamber which is connected to an output port 1501 of another fluid pump 1201 through a tubing 901. The pump 1201 is constructed in the same manner and to the same size as the pump 12. A pressure in the actuating chamber of the heart 101 is detected by a pressure sensor 6101, a signal or voltage from which is applied to a pumping controller 4201.

Figure 2B:
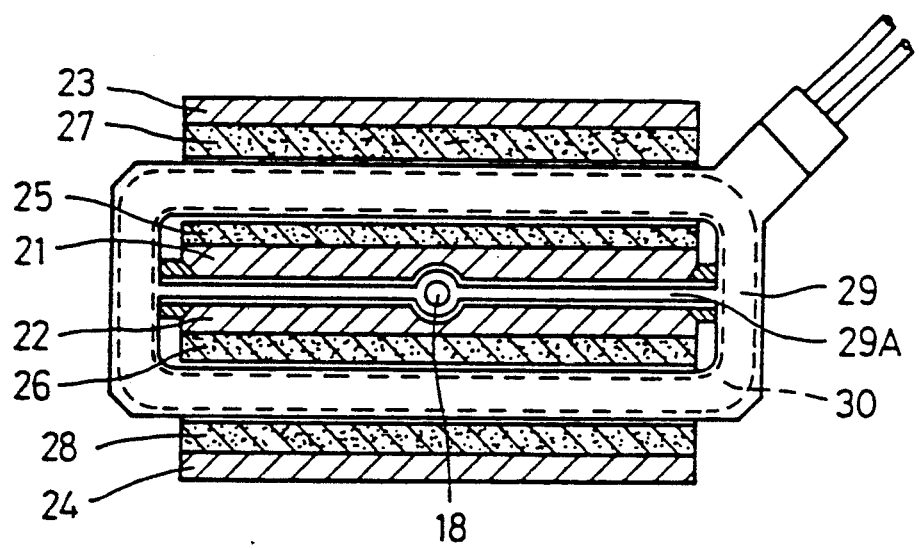

FIG. 2a shows the fluid pump 12 in a longitudinal section, to an enlarged scale while FIG. 2b shows a cross section taken along the line IIB—IIB shown in FIG. 2a. Referring to these Figures, an end member 14 in which a fluid output port 15 is formed is secured to a ring 13 together with an outer casing 16. The right end of a substantially cylindrical bellows 19 is also secured to the ring 13. A partition member 17 is secured to the left end of the bellows 19. A combination of the end member 14, the bellows 19 and the partition member 17 defines a fluid space 50 which communicates with the output port 15.

A rod 18 has its right end secured to the center of the partition member 17, and when the rod 18 is driven for reciprocating motion in the left and right direction, the fluid space 50 may be deflated and inflated, whereby silicone oil from the fluid space 50 may be supplied to the actuating chamber 3 of the artificial heart 1 through the output port 15 or alternatively silicone oil from the actuating chamber 3 may be drawn into the fluid chamber 50 through the output port 15.

A linear motor includes an end plate 51P which is secured to the left end wall of the outer casing 16, and a pair of support plates 21, 22 of a magnetizable material, disposed in opposing relationship with each other with the center of the end plate 51P interposed therebetween, have their right ends secured to the end plate 51P, which is also formed of a magnetizable material. The left ends of the plates 21, 22 are secured to another end plate 52P, which is also formed of a magnetizable material. The support plates 21, 22 serve supporting a first and a second bearing 20A, 20B therebetween, and the rod 18 extends through these bearings. A plate-shaped permanent magnet 25 is fixedly mounted on top of the plate 21 while a plate-shaped permanent magnet 26 is secured to the lower surface of the plate 22.

A support plate 23 of a magnetizable material extends across the upper ends of the end plates 51P, 52P while a support plate 24 of a magnetizable material also extends across the lower ends of the end plates 51P, 52P, the ends of the plates 23, 24 being secured to these ends. A plate-shaped permanent magenet 27 is secured to the lower surface of the plate 23 while a plate-shaped permanent magnet 28 is secured to the upper surface of the plate 24. Left between the magnets 25 and 27 and between the magnets 26 and 28 are a space in which a coil bobbin 29 is disposed. It will be seen that the magnet 25, the plate 21, the rod 18, the plate 22 and the magnet 26 extend through the bobbin 29. The bobbin 29 carries an electric coil 30 thereon. As shown in FIG. 2b, the bobbin 29 is integrally formed with an arm 29A which extends through a clearance between the plates 21, 22, and the rod 18 is fixedly connected to the arm 29A. Accordingly, a displacement of the bobbin 29 to the right or the left causes a corresponding movement of the rod 28, whereby the partition member 17 is driven to the right or left, deflating or inflating the fluid space 50, causing silicone oil from the fluid space 50 to be supplied to the actuating chamber 3 of the artificial heart 1 through the output port 15 or causing silicone oil from the actuating chamber 3 to be drawn into the fluid space 50 through the output port 15.

The magnet 25 is uniformly magnetized so that its upper surface represents an N-pole and its bottom surface represents an S-pole. Similarly the magnet 27 is uniformly magnetized with its top surface representing an N-pole and its bottom surface representing an S-pole. The space left between the magnets 25 and 27 in which the coil 30 is movable can be activated to define a substantially uniform magnetic field or parallel field which represents an N-pole on the side located adjacent to the magnet 25 and which represents an S-pole on the side located adjacent to the magnet 27. Thus it will be seen that a magnetic flux passes through a magnetic path including the upper surface of the magnet 25, the lower surface of the magnet 27, the upper surface of the magnet 27, the support plate 23, the end plates 51P, 52P, the support plate 21, the lower surface of the magnet 25 and the upper surface of the magnet 25.

The magnet 26 is uniformly magnetized with its lower surface representing an N-pole and its top surface representing an S-pole. Similarly, the magnet 28 is uniformly magnetized with its top surface representing an S-pole and its lower surface representing an N-pole. A substantially uniform magnetic field is defined in the space left between the magnets 26 and 28 in which the coil 30 is movable, with the side located adjacent to the magnet 26 representing an N-pole and the side located adjacent to the magnet 28 representing an S-pole. A magnetic flux passes through a magnetic path including the lower surface of the magnet 26, the upper surface of the magnet 28, the lower surface of the magnet 28, the support plate 24, the end plates 51P and 52P, the support plate 22, the upper surface of the magnet 26 and the lower surface of the magnet 26.

Assuming that in the region between the magnets 25 and 27, a current flows through the coil 30 in a direction from the front side to the back side of the sheet of the drawing as viewed in FIG. 2a (a current in the positive direction), it follows from Flemming's left-hand rule that portions of the coil 30 located between the magnets 25 and 27 and between the magnets 26 and 28 are subject to an electromagnetic force tending to drive it to the right, whereby the coil 30 and hence the bobbin 29 will be driven to the right, as viewed in FIG. 2a, thus driving the rod 18 to the right (drive stroke). If a current flows through the coil 30 in the opposite direction, the bobbin 29 will be displaced to the left, driving the rod 18 to the left (suction stroke).

Figure 3:
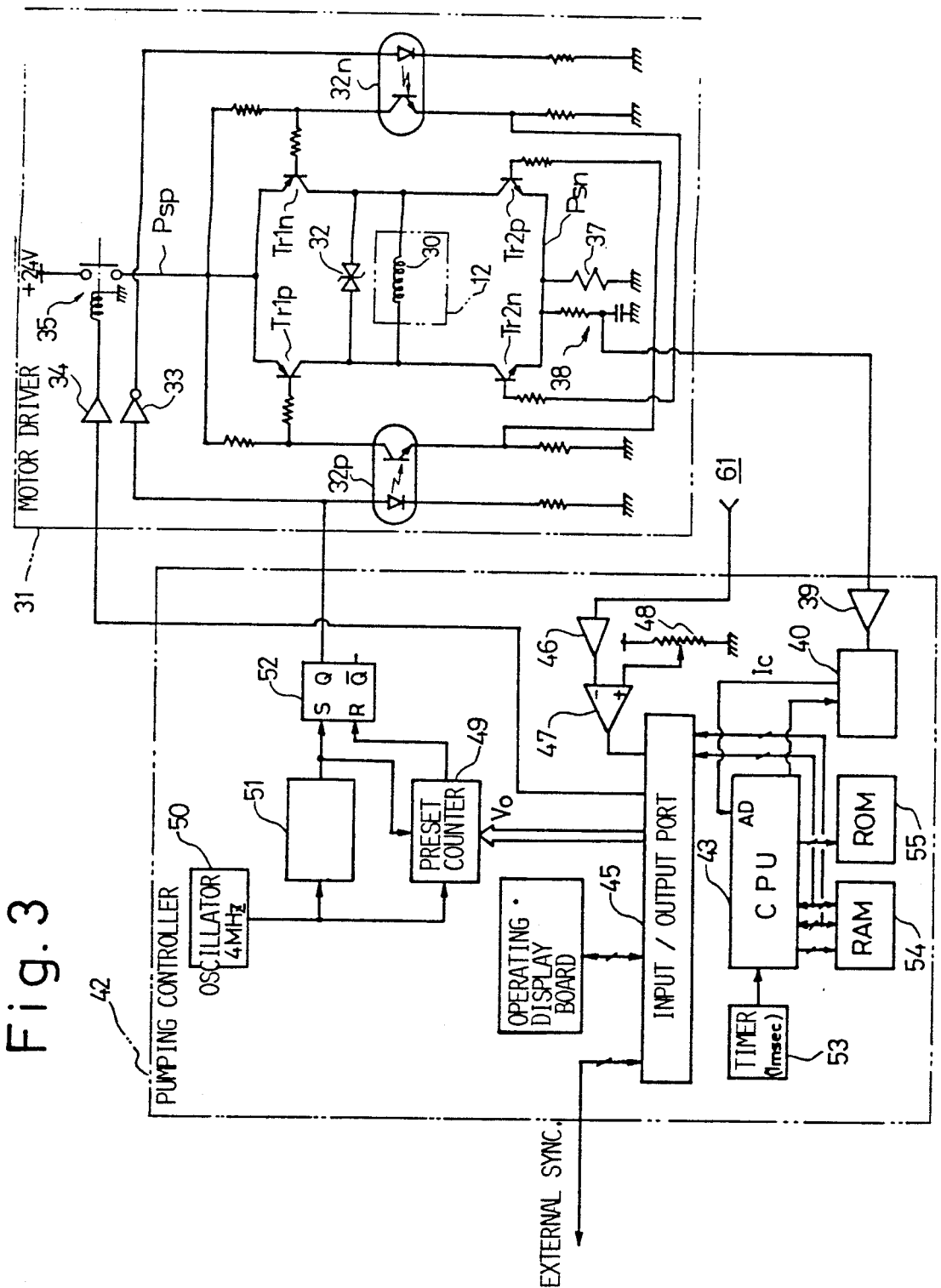
FIG. 3 is a circuit diagram of a motor driver 31 and a pumping controller 42 shown in FIG. 1.

The coil 30 is connected to a motor driver 31, which is shown in FIG. 3 together with a pumping controller 42 which controls the energization thereof.

Referring to FIG. 3, the coil 30 of the linear motor has its one end connected to a positive bus Psp or a negative bus Psn through a switching transistor Pr1$p$ or Pr2$n$ while the other end of the coil is connected to the positive bus Psp or a negative bus Psn through a switching transistor Pr1$n$ or Pr2$p$. The coil 30 is shunted by a Zener diode 32 which serves bypassing a voltage surge. The positive bus Psp is connected to a power terminal feeding +24 V through relay contacts 35 while the negative bus Psn is connected to the electric ground of the apparatus through a current detecting resistor 37 having a reduced resistance. The relay 35 includes a coil which is connected to a relay driver or amplifier 34.

The pumping controller 42 includes an R/S flipflop 52, and when its output Q assumes a high level H, a light emitting diode in a photocoupler 32$p$ becomes activated to render the switching transistors Pr1$p$ and Pr2$p$ conductive, thus allowing a current flow in a positive direction through the coil 30. This causes the coil 30 to be displaced to the right as viewed in FIG. 2a, whereby silicone oil from the fluid space 50 is discharged through the output port 15 (positive pressure interval or discharge interval). When the output Q from the flipflop 52 is at its high level H, it is inverted by an inverter 33 before it is applied to a photocoupler 32$n$, so that a light emitting diode therein is not activated for illumination, and the switching transistors Tr1$n$ and Tr2$n$ remain non-conductive.

When the output Q from the flipflop 52 changes to its low level L, the inverter 33 supplies an H level output, thus illuminating the diode in the photocoupler 32$n$ and rendering the switching transistors Tr1$n$ and Tr2$n$ conductive. This brings forth a current flow in the opposite direction through the coil 30, whereby the coil 30 is displaced to the left, as viewed in FIG. 2a, thus drawing silicone oil into the fluid space 50 through the output port 15 (negative pressure interval or suction interval).

The current flow through the coil 30 also passes through the resistor 37, and a voltage thereacross which is proportional to a current flow Ic is passed through a low pass filter 38 to be applied to an amplifier 39 of the pumping controller 42 where a level conversion is made and thence fed to sample-and-hold circuit 40. The voltage which is held by the circuit 40 is subject to an analog-to-digital conversion by CPU (microprocessor) 43 and written thereinto. It is to be noted that a switching signal to the relay 35 is supplied from CPU 43 to the motor driver 31.

The pumping controller 42 includes an operating and display board 44 in addition to CPU 43. While not shown, the board 44 is provided with a number of key switches which are used to instruct an adjustment of various driving parameters, a key switch which commands an operation start, a key switch which commands the operation to be stopped, and various indicators which indicate the prevailing values of the individual parameters. Adjustable parameters include a force with which a driving liquid such as silicone oil to be supplied to the artificial heart 1 is driven (current level in the positive or negative polarity), an interval during which a positive pressure is supplied and a pulsating period. In this example, timings when a positive or a negative pressure is supplied to the artificial heart 1 can be changed between an internal synchronization in which such timings are determined internally within CPU 43 or an external synchronization shown in FIG. 3 in which these timings are synchronized with an externally applied sync signal.

In the present embodiment, the current level which is used to energize the coil 30 is determined in a manner such that a positive current is passed through the coil 30 during an interval Tt of one period T (64 $\mu$sec) and a negative current is passed therethrough during an interval (T−Tt), a ratio Tt/T determing the energization level. By way of example, as illustrated in FIG. 6, the output Q from the flipflop 52 may be switched btween H and L levels in the period T. When the H interval Tt is successively reduced, it will be seen that when the output Q assumes its H level, a voltage of +24 V which serves energizing the coil to the positive polarity is applied while when the output Q assumes its L level, a voltage of −24 V which serves energizing the coil to the negative polarity is applied, so that a mean voltage, or a voltage which is smoothed over a time sequence gradually changes from a positive to a negative polarity. A corresponding current passes through the coil 30. Thus, a kind of duty cycle control is employed in this embodiment in determining the magnitude and the polarity of the energizing current for the coil 30.

The period T of the duty cycle control is chosen equal to 64 $\mu$sec. Specifically, pulses produced by 4 MHz oscillator 50 are counted by a cyclic counter 51 which is reset to a count 0 upon reaching a count of 256. A carry pulse from the counter 51, or a pulse having a duration of 0.25 $\mu$sec which is produced by the oscillator 50 and which is developed when the counter has counted 256 such pulses (period T=0.25 $\mu$sec×256=64 $\mu$sec) is used to set the flipflop 52. The interval Tt of the period T which is used for the energization to the positive polarity is determined by supplying data $V_0$ representing the interval Tt to a preset counter 49. In response to a carry pulse from the counter 50, the counter 49 is loaded with data $V_0$, and then operates to count down pulses produced by the oscillator 50. When data $V_0$ has been completely counted down or the count in the counter 49 reaches zero, it produces a borrow pulse, which is used to reset the flipflop 52. Accordingly, the length of the interval Tp which is chosen for the energization to the positive polarity with respect to the period T or the duty cycle can be changed, by changing data $V_0$ applied to preset data input of the counter 49 which is fed from CPU 43 through an input and output port 45.

The pulsating period may be determined by an externally applied sync signal (external synchronization mode). Alternatively, it may be determined in accordance with pulsating period data Tc (in units of msec) which is supplied from the operating and display board 44 (internal synchronization mode). During the internal synchronization mode, CPU 43 executes an interrupt operation in response to a time-over signal (carry pulse) produced by a timer 53 for each 1 msec time interval elapsed. During the interrupt operation, the number of time-over signals is counted until a count Tc is reached, whereupon data $V_0$ preset into the counter 49 is changed to a drive voltage Vp for the discharge interval (8 bit data representing Tp), thus clearing or initializing the count in the counter. During the external synchronization mode, such switching operation takes place in response to an oncoming sync signal which is externally applied.

Considering the discharge stroke of the rod 18, as long as $V_0$=Vp is applied to the preset counter 49, the current Ic passing through the coil 30 is integrated. When the integrated value reaches a value Lp which is specified for the discharge stroke and which is entered previously from the board 44 or when the discharge interval has been terminated, CPU 43 then performs the aforementioned interrupt operation to decrement preset data $V_0$ by one, thus stepwise diminishing the duty cycle. As shown in FIG. 6, the voltage applied across the coil 30 is between +24 V and −24 V, and there are 256 steps corresponding to a maximum value represented by 8 bit data therebetween. Accordingly, one step represents 48/256 V. Since each interrupt operation decrements the preset data $V_0$ by one, the voltage will be reduced at a rate equal to (48/256)×1000 V/sec. The decrementing operation of the preset data $V_0$ is terminated when the preset data $V_0$ becomes equal to or reduces below a value Vn which is specified for a minimum pressure for the suction interval or a maximum pressure during the suction interval if considered in its absolute magnitude and which is entered from the board 44. If a detected pressure from the pressure sensor 61 becomes equal to or reduces below a preselected pressure (it being noted that the detected pressure is a negative pressure since this occurs during the suction interval. If represented in the absolute magnitude of the pressure, such detected pressure will be above the preselected pressure) before the data $V_0$ reduces below the specified value Vn, the decrementing of the data $V_0$ is terminated until the detected pressure exceeds the preselected pressure.

It should be noted that a motor driver 3101 shown in FIG. 1 remains the same as the motor driver 31 as is a pumping controller 4201 which remains the same as the pumping controller 42.

Figure 4:
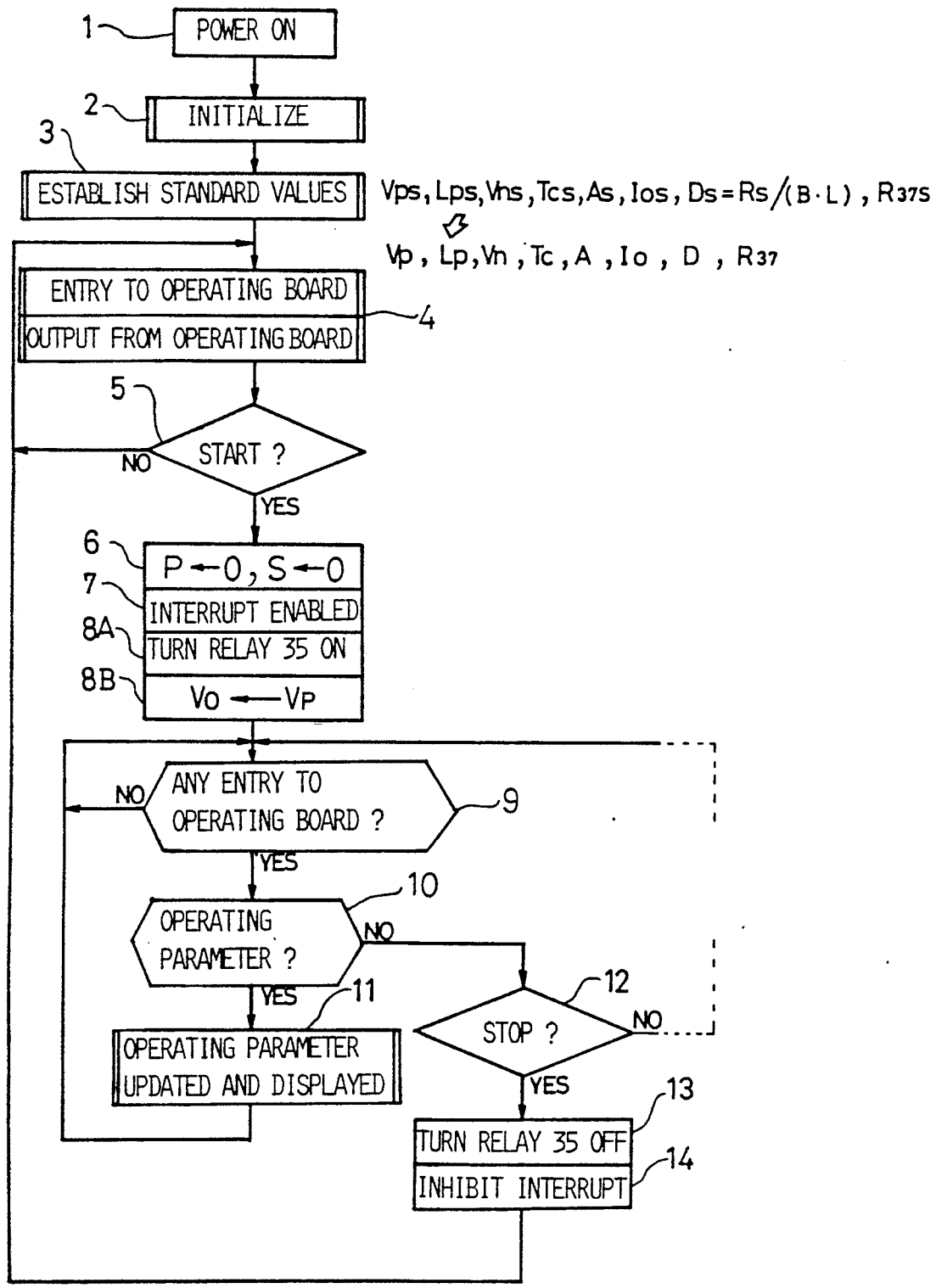
FIG. 4 is a flow chart illustrating a control operation performed by a microprocessor 43 shown in FIG. 3.

FIG. 4 shows a control operation performed by CPU 43 shown in FIG. 1. Specifically, when the power supply is turned on at step 1, an initialization takes place within CPU 43 at step 2. Thus, internal memories are cleared, standby levels are delivered to output ports, and predetermined initial values or standard values are written into selected parameter regions or registers of the internal memories.

At initialization step 2, a standard value Vps is written into register Vp into which voltage data Vp, to be applied to the coil 30 during the discharge interval, is to be written. Such data represents the length of the interval Tt during which the mean voltage Vp is applied across the coil 30. This is represented in units of the pulse period 0.25 μsec from the oscillator 50, and is formed as 8 bit data representing the count of pulses. A standard value Lps is written into a register Lp into which discharge stroke (discharge interval) data Lp is to be written. A standard value Vns is written into register Vn into which voltage data Vn (8 bit data similar to Vp) which is to be applied across the coil 30 during the suction interval is to be written. A standard value Tcs is written into a register Pc into which the pulsating period data Tc (in units 1 msec, representing the number of times the timer 53 has timed out) is to be written during the internal synchronization mode. A standard value As (As=1) is written into a register A into which a coefficient data A which is used to correct an error in a stroke calculated value which may be caused by a change in the resistance with a temperature change of the coil 30 (A=R/Rs; R representing a prevailing coil resistance and Rs representing a coil resistance at a standard temperature) is to be written. A standard value $I_0s$ is written into a register $I_0$ into which a current level $I_0$ which prevails immediately before the coil 30 initiates its displacement (namely, a maximum current level at which the coil 30 can remain stationary as the current level is gradually increased) is to be written. A standard value Ds=Rs/(B·L) is written into a register D into which data D representing R/B·L used in the equation for calculating the stroke is to be written. Finally, a standard value $R_{37}s$ is written into a register $R_{37}$ into which the resistance $R_{37}$ of the coil current detecting resistor 37 is to be written.

Upon completion of the initialization step 2, CPU 43 reads various key switches on the board 44, changes preset values (content of various registers) in accordance with the inputs, and display the preset values of these parameters on the operating board 44 at step 4.

When the start key switch on the board 44 is operated, CPU 43 clears a register P which counts the number of pulsations only once as well as a register S which stores data indicating if it is now a discharge interval or suction interval at step 6. It then enables an interrupt operation at step 7. The relay 35 is energized to connect the positive bus Psp to +24 V supply terminal at step 8A, and the preset counter 49 is loaded with $V_0=Vp$ at step 8B. In this manner, the voltage Vp which is to be used during the discharge interval is applied across the coil 30, and the positive current passes through the coil 30. (As described previously, the fluid space 50 in FIG. 2a is deflated, whereby a high pressure is applied to the artificial heart 1.)

Figure 5:
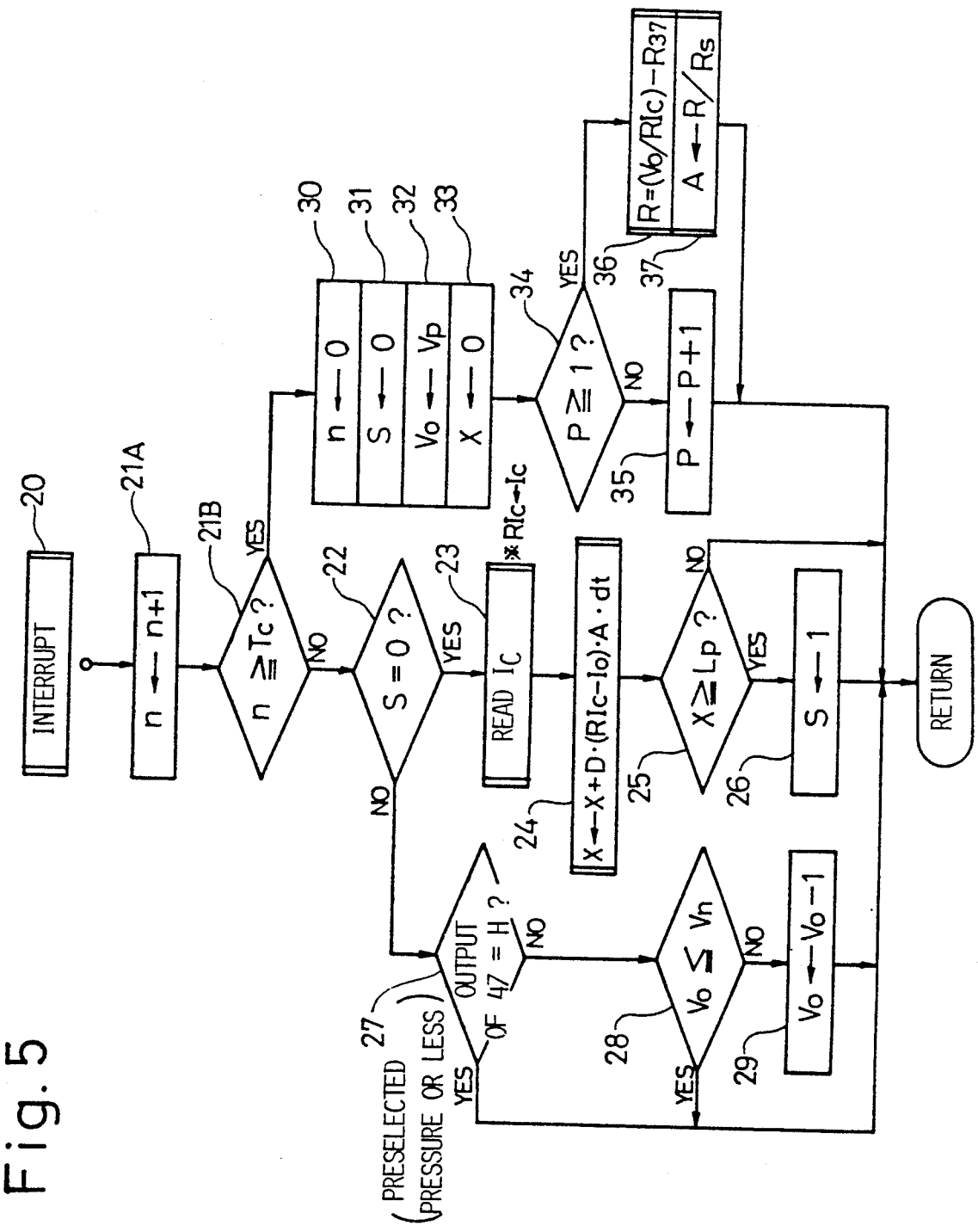
FIG. 5 is a flow chart illustrating an interrupt operation performed by the microprocessor 43.

When the interrupt operation is enabled at step 7, CPU 43 executes an interrupt operation (subroutine 20) shown in FIG. 5 as the timer 53 produces a time-over signal for each 1 msec interval elapsed.

Subsequently, CPU 43 returns to the main routine shown in FIG. 4, and waits for new inputs supplied to the board 44. Step 9. When a new input is supplied, if it represents an operating parameter, the register which stores such parameter is updated with the new input, with a corresponding display, at steps 10 and 11. When a stop input is entered, the relay 35 is deenergized, whereby the motor driver 31 is turned off to stop the linear motor 12. Steps 12 and 13. An interrupt operation is inhibited at step 14. Since the interrupt operation is inhibited, CPU 43 ceases the execution of the interrupt operation shown in FIG. 5. CPU 43 then waits for a start input at steps 4 and 5.

Referring to FIG. 5 which shows an interrupt subroutine 20, a pumping control by CPU 43 will now be described. It is to be understood that the interrupt subroutine 20 is executed in response to a time-over signal from the timer 53 which is produced with a period of 1 msec. Note in particular that the execution occurs in the period of 1 msec. It is also to be noted that the interrupt subroutine 20 is executed when the internal synchronization mode is specified. If the external synchronization mode is chosen, when the main routine (FIG. 4) waits for an input on the operating board at step 9, a signal representing any oncoming external sync signal is written into a selected register G, and in the interrupt operation, a reference is made to the content of this register G instead of steps 21A and 21B in FIG. 5, and the register is cleared in response to such external sync signal, whereupon the program proceeds to step 30 to be described later. In the absence of any oncoming external sync signal, the program proceeds to step 21B to be described later. In other respects, the control operation remains the same between the internal and the external synchronization mode.

(1) Control of discharge interval for the first pulsation responsive to the start input at step 5 which occurs subsequent to the turn-on of the power supply at step 1.

Since the register P has been cleared at step 6, its content P is equal to 0. The fact that P=0 indicates that the first pulsating period has not passed since the start of the pumping drive. Since the register S has also been cleared at step 6, its content S is equal to 0. The content S indicates whether it is the discharge or the suction interval. S=1 indicates the suction interval while S=0 indicates the discharge interval. When the program proceeds to the interrupt subroutine 20 during the internal synchronization mode, CPU 43 increments a count register n by one at step 21A, examines if the count n is equal to or greater than the pulsation period Tc at step 21B, and if the period is not reached, it refers to the content of the register S at step 22. Since S=0, it reads the current level Ic through the coil 30 at step 23. At this time, a holding command is applied to the sample-and-hold circuit 40 to cause it to retain the prevailing current detecting signal, which is then supplied to an analog signal input port AB for A/D conversion. The resulting digital value is read, and is written into register RIc.

Then CPU 43 calculates a displacement of the coil 30 or the rod 18; $(D \cdot RIc - I_0) \cdot A \cdot dt$ where $dt = 1$ msec, and adds it to the content of register X for purpose of integration, with a resulting sum used to update the register X at step 24. In other words, the displacement of the rod 18 is calculated and the content of the register X is updated to the calculated value. It is to be noted that D, RIc, $I_0$ and A represent the contents of registers D, RIc, $I_0$ and A mentioned previously. RIc represents the prevailing coil current Ic.

CPU 43 then examines to see if the content of the register X, representing the displacement of the rod 18 to the right, is equal to or greater than the content of the register Lp, which represents the preset value for the stroke by which the rod 18 is to be driven to the right or the discharge interval at step 25. If not, the program returns to the main routine shown in FIG. 4. In this manner, each time the interrupt subroutine 20 is entered, the program proceeds to steps 21A, 21B, 22, 23, 24 and 25 and then returns to the main routine.

Upon reaching $X \geq Lp$, indicating that the discharge interval of the first pulsation has been completed subsequent to the start command, the register S is updated to 1 representing the suction interval at step 26.

(2) Control of the suction interval of the first pulsation responsive to the start input at step 5 subsequent to the turn-on of the power supply at step 1.

It should be noted initially that the content of the register P is equal to 0 while the content of the register S is equal to 1. Upon entering the interrupt subroutine 20, the program proceeds through steps 21A, 21B, 22 and 27 where an output from a comparator 47 is examined at step 27. It is also examined to see if output data $V_0$ to be delivered to the preset counter 49 is equal to or less than voltage $V_n$ corresponding to the minimum pressure during the suction interval at step 28. An output from the comparator 47 assumes an H level when the detected pressure from the pressure sensor 61 is equal to or less than a pressure value which is established by a potentiometer 48, indicating that the absolute value of the negative suction pressure is above a preselected value, thus indicating a suction over-pressure, and assumes an L level when the detected pressure exceeds the preselected pressure, indicating that the absolute magnitude of the negative suction pressure is less than the preselected value, indicating a valid suction pressure. If an output from the comparator 47 is at its L level and $V_0$ is greater than $V_n$, indicating that the voltage across the coil has not been reduced to the minimum voltage $V_n$ which is to be used during the suction interval, data $V_0$ is decremented by one and is loaded into the preset counter 49 at step 29. In this manner, during the interrupt subroutine 20, the step 21A, 21B, 22, 27, 28 and 29 are executed as long as the absolute magnitude of the suction pressure is less than the preselected pressure, as considered in absolute magnitude, and the voltage across the coil has not been reduced to $V_n$. When the content of the count register n becomes equal to or greater than Pc, indicating that the suction interval has been terminated, the register n is cleared at step 30, the register S is cleared at step 31, the preset data $V_0$ to the counter 49 is updated to $V_p$ which specifies a coil voltage to be used during the discharge interval at step 32, the stroke register X is cleared at step 33, and since the content of the register P is now equal to 0, this register is incremented by one at steps 34 and 35.

(3) Control of discharge interval during a second and subsequent pulsation; similar to the control mentioned under the paragraph (1).

(4) Control of suction interval during a second and subsequent pulsation;

The control which takes place while the count register n is less than Tc remains the same as the control mentioned under paragraph (2). However, when n becomes equal to or greater than Tc, the resistance R of the coil 30 is calculated at step 36: $R = V_0/RIc - R_{37}$ where it will be understood that $V_0$ represents the voltage applied across the coil, RIc represents the content of register RIc which represents the current Ic through the coil 30 at the end of the discharge interval and $R_{37}$ represents the content of register $R_{37}$ indicating the resistance of the register 37. CPU 43 then calculates a correction coefficient $A = R/R_s$, which is used to update the register A at step 37. It will be understood that Rs represents a standard resistance of the coil 30. The correction coefficient A which is updated in this manner is used in a calculation of the stroke X for the next discharge interval at step 11. The purpose of calculating the resistance R is to compensate for any inaccuracy which may be caused in the calculated value of the stroke X for the discharge interval determined by the coil current Ic as a result of a temperature change of the linear motor 12 to vary its resistance R.

Immediately after the start, the position of the rod 18 remains uncertain. If the initial position of the rod 18 is shifted to the right, during the energization to the positive polarity or the energization for the discharge interval, the bellows 19 may be excessively compressed, whereby the rod 18 may cease to move to the right while the energization is continued. Conversely, if the initial position of the rod 18 is shifted to the left, the discharge interval may have been terminated before the bellows 19 is effectively compressed, and thus the energization to the positive polarity may have been terminated while the bellows 19 is still compressible. Accordingly, it is expected that variations will occur in the load and the speed of the movement of the coil 30 during the discharge interval of the first pulsation which immediately follows the start. For this reason, the calculation of the resistance R of the coil 30 based on the detected current RIc during the discharge interval of the first pulsation which takes place at step 36 normally as well as a modification of the correction coefficient A based on such resistance which takes place at step 37 are not executed.

Similarly, at the end of the suction interval of a third and subsequent pulsation when n becomes equal to or greater than Tc, the calculation of the resistance R (step 36) and the modification of the correction coefficient A (step 38) are executed, and the calculation of the stroke X based on the calculated correction coefficient A which takes place at step 24 is initiated, beginning with the discharge interval of the third pulsation. In the calculation of stroke X for the discharge interval of the first and the second pulsation, the correction coefficient A=As which is stored in the register is used in the calculation.

As mentioned above, the current Ic through the coil 30 is integrated (step 24) to calculate the stroke X for the rod 18, and when it reaches the preselected value Lp, a switching from the discharge to the suction stroke takes place. Accordingly, by adjusting the preselected value Lp and the voltage Vp applied for the discharge interval, the discharge flow rate of the liquid pump 12 or the artificial heart 1 may be adjusted. Such adjustment can be made by a key operation on the board 44 to change the content of the registers Lp and/or Vp in the present embodiment. In this manner, the discharge flow rate can be adjusted without using position detecting means such as a potentiometer.

Since the correction coefficient A used in the equation to calculate the stroke at step 24 is updated at step 37 in a manner corresponding to the resistance R of the coil 30 which is detected at step 36, or stated differently, the equation is modified in a manner corresponding to a variation in the resistance R of the coil 30 which is principally attributable to a temperature change, an accurate stroke or discharge flow rate can be maintained in the presence of a change in the resistance of the coil 30 which is caused by a temperature change.

During the discharge interval, the voltage $V_0$ applied across the coil (which is data Tp shown in FIG. 6, producing a mean voltage applied across the coil 30 in a manner depicted in FIG. 6) remains constant at Vp, but when a switching from the discharge interval to the suction interval is made, the voltage $V_0$ applied across the coil is stepwise decremented for each millisecond elapsed, whereby the voltage is gradually reduced at a rate of $(48/256) \times 1000$ V/sec from a positive value, passing through 0 and continuing in the negative direction, thus causing a gradual increase in the negative current. When $V_0$ is changed to Vn, which is a specified value for the suction voltage, the decrementing of the voltage is interrupted at steps 28, 29. In the event the pressure detected by the sensor 61 becomes equal to or reduces below a preselected value and an output from the comparator 47 changes to its H level while the voltage is gradually reduced from a positive value toward a negative value and then increase in the negative direction or while the suction pressure is gradually increased, the decrementing of the voltage $V_0$ or a gradual increase in the negative current is terminated (a jump from step 27 to Return). When it reduces below the preselected value, the voltage is changed or the negative current is gradually increased at steps 27, 28 and 29.

If the rate at which the blood is collected to the distal end of the canule 7 is retarded relative to an increase in the suction pressure during the suction interval and/or tissues of a living body are located too close to the distal end of the canule, during the suction stroke of the pumping apparatus, the deflation of the volume of the space in the actuating chamber 3 of the artificial heart 1 will be retarted relative to the rate at which the suction pressure from the output port 15 of the pumping apparatus increases, causing an increase in the suction pressure from the port 15 of the actuating chamber 3. However, at this time, the pressure detected by the pressure sensor 61 reduces below a preset value, indicating that the suction pressure is equal to or above a preselected value, whereby an output from the comparator 47 changes from its L to its H level. In response thereto, CPU 43 interrupts the decrementing of the voltage $V_0$ or a gradual increase of the negative current. Accordingly, the rate at which the suction pressure increases is reduced, allowing the blood collection to the distal end of the canule to proceed with a concomittant pressure rise from the output port 15 of the actuating chamber 3 or a reduction in the suction pressure. When an output from the comparator 47 changes from its H to its L level in response to the reduction in the suction pressure, CPU 43 resumes the decrementing of the voltage $V_0$ or a gradual increase of the negative current, unless $V_0$ has been reduced to or below Vn. In this manner, the likelihood that the heart of a living body may be damaged as a result of its being strongly attracted to the canule 7 can be greatly reduced. By way of example, FIG. 7 graphically shows such likelihood. Assuming that voltage data Vp which is to be used during the discharge interval is chosen so as to furnish a positive pressure substantialy on the order of 100 mmHg to the artificial heart 1 and voltage data Vn which is to be used during the suction interval is chosen to furnish a negative pressure on the order of $-50$ mmHg, at the termination of the discharge interval without utilizing a detected pressure from the pressure sensor 61, the voltage applied across the coil may be continuously changed from Vp to Vn at a rate of $(48/256) \times 1000$ V/sec. In this instance, if the rate of blood collection to the distal end of the canule 7 is slow or the wall of the heart is located too close to the distal end of the canule 7, a curve P shown in FIG. 7 indicates that the negative suction pressure which prevails at the canule 7 may reach $-100$ mmHg. However, if the preselected pressure of $-50$ mmHg is established by the potentiometer 48 in accordance with the invention so that the decrementing of the voltage $V_0$ applied across the coil may be interrupted at the detected pressure from the pressure sensor 61 which is equal to or below $-50$ mmHg, the negative suction pressure which prevails at the canule 7 will be suppressed to the order of $-50$ mmHg or more exactly, to the order of $-60$ mmHg at its bottom peak, as indicated by a curve I in FIG. 7, thus preventing an excessive suction pressure (which may be as high as $-100$ mmHg) from being applied to the distal end of the canule 7.

It should be understood that the liquid pump instead of the rod 18 and the bellows 19 used as the reciprocable members, the outer casing 16 may be replaced by a cylinder and the bellows 19 may be replaced by a piston.

While a preferred embodiment of the invention has been illustrated and described, it is to be understood that there is no intention to limit the invention to the precise constructions disclosed herein and that the right is reserved to all changes and modifications coming within the scope of the invention as defined in the appended claims.

What is claimed is:

1. Pumping apparatus comprising
 a liquid pump including an electric linear motor, and a reciprocable member communicating with a fluid output port and driven for reciprocating motion by the linear motor to deflate/inflate a fluid space in which a non-compressible liquid is contained;
 pressure detecting means for detecting a pressure at the fluid output port;
 energization means for alternately energizing the coil to the positive/negative polarity;
 current detecting means for detecting the current which passes through the coil;
 and current control means for defining the current levels which are used by the energization means to energize the coil to the positive/negative polarity, the current control means operating such that at least during one of the energization to the positive/negative polarity, it integrates the current detected by the current detecting means until an integrated current valve reaches a given value, whereupon the polarity of energization is reversed, the current control means also operating such that during at least one of the energization to the positive/negative polarity, the energization means is caused to increase the current level which is used to energize the coil to a given value gradually, and the gradual increase is interruped whenever the pressure detected by the pressure detecting means has gone out of a given range in the process of the gradual increase.

2. Pumping apparatus according to claim 1 in which the current control means calculates a resistance of the coil based on the voltage applied across the coil and the current detected by the current detecting means, the control means correcting the integrated current value in a manner corresponding to the ratio of the resistance to a standard value.

3. Pumping apparatus according to claim 1 in which the energization means comprises positive switching means for energizing the coil to the positive polarity, negative switching means for energizing the coil to the negative polarity, timing signal generating means for generating a positive on command signal with a given short period and for generating a negative on command signal at a positive on interval indicated by a positive on interval information after the occurrence of the positive on command signal, and means responsive to the positive on command signal to turn the positive switching means on and to turn the negative switching means off and also responsive to the negative on command signal to turn the positive switching means off and to turn the negative switching means on, the current control means delivering the positive on interval information which specifies the current level to be used for the energization to the positive polarity to the timing signal generating means with a give long period, the control means gradually decreasing the positive on interval information when the integrated current value has reached the given value subsequent to the delivery and ceasing the gradual decrease when the pressure detected by the pressure detecting means goes out of a given range and terminating the gradual decrease when the positive on interval information has been gradually reduced to the given value.

4. Pumping apparatus comprising
a liquid pump including an electric linear motor, and a reciprocable member communicating with a fluid output port and driven for reciprocating motion by the linear motor to deflate/inflate a fluid space in which a non-compressible liquid is contained;
pressure detecting means for detecting a pressure at the fluid output port;
current detecting means for detecting a current which passes through the coil;
positive switching means for energizing the coil to the positive porality;
negative switching means for energizing the coil to the negative polarity;
timing signal generating means for generating a positive on command signal with a given short period and for generating a negative on command signal at a positive on interval indicated by positive on interval information after the occurrence of the positive on command signal;
means responsive to the positive on command signal to turn the positive switching means on and to turn the negative switching means off and also responsive to the negative on command signal to turn the positive switching means off and to turn the negative switching means on;
and current control means for delivering the positive on interval information which specifies the current level used to energize the coil to the positive polarity to the timing signal generating means with a given long period, for integrating the current value detected by the current detecting means since the delivery until the integrated value reaches a given value, whereupon it initiates a gradual decrease of the positive on interval information, for ceasing the gradual decrease whenever the pressure detected by the pressure detecting means goes out of a given range, and for terminating the gradual decrease when the positive on interval information has been gradually reduced to a given value.

5. Pumping apparatus according to claim 4 in which the current control means calculates a resistance of the coil based on the voltage applied across the coil and the current detected by the current detecting means, and corrects the current which is to be integrated in a manner corresponding to the ratio of the resistance to a standard value.

6. Pumping apparatus according to claim 4 in which the liquid which is contained in the fluid space is silicone oil.

7. Pumping apparatus comprising
a liquid pump including an electric linear motor, and a reciprocable member communicating with a fluid output port and driven for reciprocating motion by the linear motor to deflate/inflate a fluid space in which a non-compressible liquid is contained;
pressure detecting means for detecting a pressure at the fluid output port;
energization means for alternately energizing the coil to the positive/negative polarity including positive switching means for energizing the coil to the positive polarity, negative switching means for energizing the coil to the negative polarity, timing signal generating means for generating a positive on command signal with a given short period and for generating a negative on command signal at a positive on interval indicated by a positive on interval information after the occurrence of the positive on command signal, and means responsive to the positive on command signal to turn the positive switching means on and to turn the negative switching means off and also responsive to the negative on command signal to turn the positive switching means off and to turn the negative switching means on;
and current control means for defining the current level at which the energization means energizes the coil to the positive/negative polarity, the control means operating in a manner such that during at least one of the energization to the positive/negative polarity, the energization means gradually increases the current level which is used to energize the coil to a given value, and to interrupt the gradual increase whenever the pressure detected by the pressure detecting means goes out of a given range in the process of gradually increasing the current level;
the current control means delivering the positive on interval information which specifies the current level to be used for the energization to the positive polarity to the timing signal generating means with a given long period, the control means gradually decreasing the positive on interval information after the reciprocable member has forwardly moved through a given stroke subsequent to the delivery and ceasing the gradual increase when the pressure detected by the pressure detecting means goes out of a given range and for terminating the gradual increase when the positive on interval information has been gradually reduced to the given value.

* * * * *